United States Patent [19]

Valdiserri et al.

[11] 4,376,857

[45] Mar. 15, 1983

[54] PHOSPHITE-ISOCYANURATE OLIGOMERS

[75] Inventors: Leo L. Valdiserri; Richard P. Woodbury, both of Belpre, Ohio

[73] Assignee: Borg-Warner Corporation, Chicago, Ill.

[21] Appl. No.: 298,967

[22] Filed: Sep. 3, 1981

[51] Int. Cl.$^3$ .................. C07D 403/12; C07D 403/14
[52] U.S. Cl. .................................................. 544/214
[58] Field of Search ........................................ 544/214

[56] References Cited

U.S. PATENT DOCUMENTS

| | | | |
|---|---|---|---|
| 3,121,082 | 2/1964 | Guttag | 544/214 |
| 4,085,283 | 4/1978 | Den Otter et al. | 544/214 |
| 4,096,114 | 6/1978 | Minagawa et al. | 544/214 |
| 4,287,339 | 9/1981 | Valdiserri | 544/214 |

FOREIGN PATENT DOCUMENTS

| | | |
|---|---|---|
| 54-7935951 | 2/1979 | Japan . |
| 54-7930241 | 3/1979 | Japan . |
| 1526603 | 9/1978 | United Kingdom . |

*Primary Examiner*—John M. Ford
*Attorney, Agent, or Firm*—Joseph Shekleton

[57] ABSTRACT

Certain phosphite-isocyanurate oligomers and their use as thermal stabilizers in polymer compositions. The phosphite-isocyanurates may be prepared from a tris-hydroxyalkyl isocyanurate by reaction with an organic phosphite such as triphenyl phosphite or tributyl phosphite. Optionally, an alcohol such as decyl alcohol may be employed as a reactant.

7 Claims, No Drawings

PHOSPHITE-ISOCYANURATE OLIGOMERS

This invention relates as indicated to polymer stabilizers. More particularly it relates to such compositions which are phosphite-isocyanurate compounds. Still more particularly it relates to the stabilization of a wide variety of polymers, especially those which are susceptible to deterioration at elevated temperatures.

BACKGROUND OF THE INVENTION

Because of their outstanding properties, synthetic polymers are used in a wide variety of applications. They are used, for example, as fibers, films, coatings and shaped objects. In almost all of these applications, as well as in the processing of the polymers, a high degree of thermal stability is required. Many polymers are not, themselves, sufficiently stable at elevated temperatures as to resist deterioration with the result that they develop color, lose strength, etc. These polymers can be fortified against such deterioration by the addition of small proportions of certain types of compounds.

Polymers which are susceptible to deterioration at elevated temperatures and which are benefited with respect to reduced deterioration by the presence of the phosphitic-isocyanurates herein include styrene polymers such as polystyrene, high-impact polystyrene, SBR, ABS resins and MBS resins, polyamides, polycarbonates, olefin polymers such as polypropylene, low density polyethylene, high density polyethylene, polyisoprene, EPDM polymers, and copolymers of ethylene; polyvinyl chloride, polyvinyl acetate, polyvinyl ethers, polyvinyl-acetals, polyesters, polyurethanes, and polyacrylonitrile.

Japanese Patent Publication No. 79/30241 deals with this problem. It shows polyethylene and polypropylene compositions containing 2,2',2''-(1,3,5-s-triazine-2,4,6-1H,3H,5H, -trionyltris ethylene bis-(alkylphenyl)-phosphites.

The stabilization of synthetic resins in general by the presence of a small proportion of bis-(2,4-ditertiarybutylphenyl)pentaerythritol diphosphite or bis-(2-tertiarybutyl-5-methylphenyl)pentaerythritol diphosphite is shown in published Japanese application No. 79/25,951. Polyethylene stabilized compositions also contain calcium stearate, pentaerythritol tetrakis-(3,5-ditertiarybutyl-4-hydrox-phenyl propionate) and dilauryl thiodipropionate.

U.K. Pat. No. 1,526,603 shows the use of bis-(alkylphenyl)pentaerythritol diphosphites as stabilizers for polypropylene. The bis-(2,4-ditertiarybutylphenyl)pentaerythritol diphosphite is shown specifically, in combination with calcium stearate and tetrakis-methylene-3(3',5'-ditertiarybutyl-4'-hydroxyphenyl)propionate methane.

SUMMARY OF THE INVENTION

The invention of the present application is a polymer composition comprising of a major proportion of polymer and a minor proportion, sufficient to improve the stability of the polymer, of a phosphite-isocyanurate compound having the structural formula

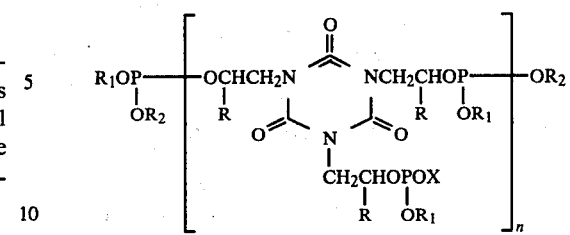

where R is methyl or hydrogen, $R_1$ and $R_2$ are alkyl radicals of 10 or more carbon atoms, phenyl or alkylphenyl radicals of 10–22 carbon atoms, X is $R_2$ or

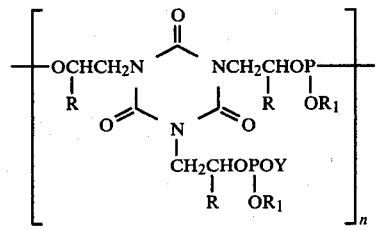

n is 2–10 and Y is $R_2$ or X.

Preferred radicals (for $R_1$ and $R_2$ in the above formula) include phenyl, 4-tertiarybutylphenyl, 2,4-ditertiarybutylphenyl, 2-methyl-4-tertiarybutylphenyl, 2,4-diisopropyl, 4-octylphenyl, 2,4-dioctylphenyl, isodecyl, n-dodecyl, tetradecyl, octadecyl and eicosyl. The hydrocarbon radicals may be the same or different. Preferably, they are different.

The value of n may as indicated range from 2 to 10; preferably, n is 2–4.

Polymer compositions containing small proportions of such oligomers are relatively stable at elevated temperatures, i.e., the melt viscosity remains fairly constant and the color is virtually unchanged.

The phosphite-isocyanurate oligomers herein may be prepared by a process comprising preparing a mixture of 1.0 mol of tris-hydroxyalkyl isocyanurate wherein the alkyl is ethyl or 2-methylethyl and from about 1.0 to about 4.0 mols of a phosphite having the structure $(RO)_3P$ wherein R is phenyl or alkyl of 1–8 carbon atoms, heating said mixture at from about 50° C. to about 200° C. to form a clear mixture and then distilling away the phenol or alcohol formed during the heating step.

The above process proceeds most efficiently in the presence of a basic catalyst. The catalyst may be a basic metal compound such as a basic metal oxide, hydroxide, carbonate, bicarbonate or alkoxide. The metal may be alkali metal or alkaline earth metal. Alternatively, the catalyst may be an amine. Tertiary aliphatic hydrocarbon amines boiling above 100° C. are particularly contemplated. Preferred catalysts are the sodium alkoxides wherein the alkoxide contains 1–4 carbon atoms.

The relative proportions of phosphite to tris-hydroxyalkyl isocyanurate ordinarily are about 3:1, on a molar basis. More phosphite than this can be used, as indicated, but the use of a large stoichiometric excess of phosphite results in the formation of a product mixture containing very little if any oligomer.

In addition to the phosphite and tris-hydroxyalkyl isocyanurate reactants as above, the process mixture may also contain an alcohol or alkylphenol containing 2–30 carbon atoms. Specific illustrative embodiments include methanol, ethanol, n-propyl alcohol, n-butyl alcohol, 2-ethylhexanol, n-decanol, undecanol-1, n-dodecanol, isododecyl alcohol, n-octadecanol, eicosyl alcohol, n-butylphenol, octadecylphenol, etc.

The temperature of the heating step may vary between 50° C. and 200° C. Preferably, the temperature is between about 80° C. and about 180° C. The process mixture becomes clear as the reaction proceeds and then the by-product phenol or alcohol as the case may be, is removed from the process mixture by distillation at reduced pressure, i.e., generally, by heating to a final temperature of, for example, 135°–180° C./0.1–0.2 mm.

The concentration of phosphite-isocyanurate in the polymer composition ranges from about 0.01 to about 1.0 pph (parts per hundred).

The polymer compositions of the invention may also contain a phenolic antioxidant, which acts to enhance the effectiveness of the phosphite additive. Illustrative phenolic compounds include phenolic esters, especially esters of 3-(3',5'-ditertiarybutylphenyl) propionic acid such as the stearyl, lauryl, ethylene, trimethylene, propylene, 1,2-hexylene, neopentyl, glyceryl and pentaerythritol esters, i.e., those having a molecular weight greater than about 425; substituted phenols and naphthols wherein the phenolic group is "hindered" by a bulky group, e.g. tertiary butyl, tertiary amyl, cyclohexyl and the like, in the ortho position, such as butylated hydroxytoluene (BHT), 2-tertiarybutyl-1-napthol, o-cyclohexylphenol, o-tertiarybutyl-phenol, etc.

The amount of phenolic antioxidant to be used in these compositions will range from about 0.01 to about 1.0 pph.

Other types of well-known polymer additives may also be used in the polymer compositions of this invention for their known purposes, including particularly metal carboxylates such as calcium stearate, magnesium stearate, zinc laurate and the like; also, oxides of these metals.

Illustrative methods of preparation are as follows:

EXAMPLE I

A mixture of 13.06 g. (0.05 mol) of tris-hydroxyethyl isocyanurate, 46.54 g. (0.15 mol) of triphenyl phosphite, 23.74 g. (0.15 mol) of decyl alcohol and 0.10 g. (0.002 mol . . . 4 mol percent of the tris-hydroxyethyl isocyanurate) of sodium methoxide is heated with stirring at 100° C. for 30 minutes. The clear reaction mixture is stripped to a final distillation temperature of 135° C./1 mm. to yield 26.72 g. of phenol. The residue is 53.93 g. of a slightly cloudy, colorless oil which is shown by high performance liquid chromatography (HPLC) to contain 75–80% of the desired oligomer, 10% of diphenyldecyl phosphite, 10% of didecylphenyl phosphite and 3–5% of decyl alcohol.

EXAMPLE II

A mixture of 13.06 g. (0.05 mol) of tris-hydroxyethyl isocyanurate, 46.54 g. (0.15 mol) of triphenyl phosphite, 47.48 g. (0.30 mol) of decyl alcohol and 0.10 g. (0.002 mol) of sodium methoxide is heated with stirring at 100° C. for 30 minutes. The clear reaction mixture is stripped to a final distillation temperature of 135° C./1 mm. to yield 42.84 g. of phenol. The residue weights 61.64 g. It contains about 10% each of tridecyl phosphite and phenyldidecyl phosphite and traces of triphenyl phosphite and decyl alcohol, the rest being the desired oligomeric polyphosphite (as shown by HPLC).

EXAMPLE III

The procedure of Example II is followed using the following amounts of reactants (no decyl alcohol is used):

13.06 g. (0.05 mol) of tris-hydroxyethyl isocyanurate
46.54 g. (0.15 mol) of triphenyl phosphite
0.10 g. (0.002 mol) of sodium methoxide The amount of phenol recovered is 11.36 g. (0.12 mol). The oligomeric product is a cloudy, colorless, very viscous liquid shown by HPLC to contain 42% of triphenyl phosphite.

EXAMPLE IV

A mixture of 6.53 g. (0.025 mol) of tris-hydroxyethyl isocyanurate, 51.60 g. (0.075 mol) of tris-(nonylphenyl) phosphite, 20.29 g. (0.075 mol) of stearyl alcohol and 0.04 g. (0.00075 mol) of sodium methoxide is heated with stirring at 125° C. for 30 minutes. The resulting clear mixture then is stripped to a final temperature of 180° C./0.15 mm. to yield 27.49 g. of nonylphenol as distillate. The residual oligomeric product is a clear yellow liquid weighing 46.29 g. It contains only traces of nonylphenol and stearyl alcohol.

EXAMPLE V

The procedure of Example IV is followed using the following amounts of reactants:

6.53 g. (0.025 mol) of tris-hydroxyethyl isocyanurate
51.60 g. (0.075 mol) of tris-(nonylphenyl) phosphite
40.75 g. (0.150 mol) of stearyl alcohol
0.04 g. (0.00075 mol) of sodium methoxide The amount of nonylphenol recovered is 41.38 g. (0.20 mol). The oligomeric product, a white waxy solid weighing 50.79 g., contains only traces of nonyl phenol, stearyl alcohol and tris-(nonylphenyl) phosphite, as shown by HPLC.

The relative stability of polymer compositions containing the phosphite-isocyanurates of this invention is shown by data obtained as follows: A mixture of 100 parts of an ABS resin (containing 30% of polybutadiene), 1.5 parts of a lubricant, 5.1 parts of titanium dioxide pigment and 0.50 part of phosphite stabilizer is processed in a Banbury mixer, then on a 2-roll mill and the resulting sheet cut into strips which are then granulated. These are injection molded into sample specimens at 450° F. and 550° F. and the color of each such specimen noted. The difference in color (between samples molded at these two temperatures) is taken as an indication of the relative stability of the compositions of the specimens. The data is shown in Table I.

TABLE I

| Phosphite | (Color Difference) |
|---|---|
| Octyl diphenyl phosphite | 4.80 |
| Product of Example I | 1.87 |

Octyl diphenyl phosphite is a well-known polymer additive, used extensively to impart desired thermal stability to ABS resins. The data above shows the clear superiority of the phosphite-isocyanurate herein as an ABS resin stabilizer.

The efficacy of the phosphite-isocyanurates as polymer additives is shown further by test data (shown in Table II) acquired by the following test procedure:

Granulated compositions as above are divided into two portions; one portion is compression molded into plaques and these plaques assigned a color rating; the other portion is extruded at 450° C. into a sheet which also is rated for color. A comparison of the two color ratings affords a measure of the stabilizing influence of the phosphite additive in the polymer sample.

TABLE II

| Phosphite | (Color Difference) |
|---|---|
| Octyl diphenyl phosphite | 5.74 |
| Product of Example I | 3.19 |

Again, the superiority as a thermal stabilizing agent of the phosphite-isocyanurates herein is clearly shown.

Further evidence of the thermal stabilizing properties of the phosphite-isocyanurates is seen in the results of a test carried out as follows: Poly(ethyleneterephthalate) (having an intrinsic viscosity of 0.59), plus phosphite-isocyanurate, is mixed at 280° C. in a Brabender mixing head. Samples are withdrawn immediately after flux and every ten minutes thereafter for 60 minutes; the color ratings of the samples reflect the various stages of deterioration and, thus, the relative effectiveness of the phosphitic-isocyanurate additives as thermal stabilizers. The color ratings are determined on the basis of a scale of 1–10, 1 being colorless and 10 being yellow-brown. The data is shown in Table III.

TABLE III

| Phosphite (phr) | Color Rating | | | | | | |
|---|---|---|---|---|---|---|---|
| | 0 | 10 | 20 | 30 | 40 | 50 | 60 |
| None | 1 | 2 | 3 | 5 | 7 | 9 | 10 |
| Product of Ex. 2 (0.2) | 1 | 1 | 1 | 2 | 2 | 3 | 6 |
| Product of Ex. 3 (0.2) | 1 | 1 | 1 | 1 | 2 | 2 | 3 |
| Product of Ex. 3 (0.05) | 1 | 1 | 2 | 3 | 4 | 6 | 8 |

The efficacy of these phosphite-isocyanurates as stabilizers in vinyl chloride polymers is shown by the data in Table IV. Rigid test samples are subjected to a Mill Stability test at 325° F., samples being removed at 5-minute intervals and rated for color. The color rating is based on a scale of 1–8 where 1 is colorless and 8 is dark brown. Each sample contains the following:

| Parts | |
|---|---|
| 100 | poly (vinyl chloride) |
| 13 | MBS (impact modifier) |
| 3 | epoxidized soya |
| 3.3 | lubes and processing aids |
| 0.3 | calcium stearate |

-continued

| Parts | |
|---|---|
| 0.15 | zinc stearate |

In addition to the above, sample B contained 0.5 parts of the product of Example 1.

TABLE IV

| Sample | (Min) | | | | | | |
|---|---|---|---|---|---|---|---|
| | 0 | 5 | 10 | 15 | 20 | 25 | 30 |
| A | 1.5 | 6 | 6 | 6 | 7 | 8 | F* |
| B | 1.0 | 2.5 | 2.5 | 2.0 | 2.0 | 2.5 | 3.0 |

*F indicates catastrophic failure of the sample.

All parts and percentages herein, unless otherwise expressly stated, are by weight.

We claim:

1. A phosphite-isocyanurate having the structure

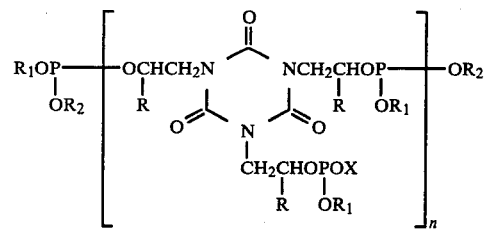

wherein R is methyl or hydrogen, $R_1$ and $R_2$ are alkyl radicals of 10 or more carbon atoms, phenyl or alkylphenyl radicals of 10–22 carbon atoms, X is $R_2$ or

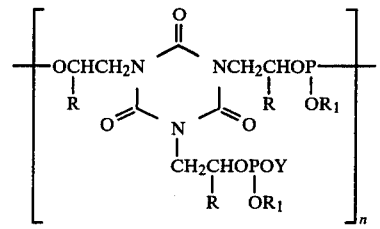

n is 2–10 and Y is $R_2$ or X.

2. The phosphite-isocyanurate of claim 1 wherein R, and $R_2$ are alkyl.

3. The phosphite-isocyanurate of claim 1 wherein $R_1$ and $R_2$ are phenyl.

4. The phosphite-isocyanurate of claim 1 wherein $R_1$ is alkyl and $R_2$ is phenyl.

5. The phosphite-isocyanurate of claim 1 wherein R is hydrogen.

6. The phosphite-isocyanurate of claim 1 wherein $R_1$ is alkyl and $R_2$ is alkylphenyl.

7. The phosphite-isocyanurate of claim 1 wherein $R_1$ and $R_2$ are alkylphenyl.

* * * * *